United States Patent [19]
Raju et al.

[11] Patent Number: 4,689,071
[45] Date of Patent: Aug. 25, 1987

[54] HERBICIDALLY ACTIVE 3-ISOXAZOLYL-2-IMIDAZOLIDINONE DERIVATIVES

[75] Inventors: Muppala S. Raju; Jerome M. Lavanish, both of Akron, Ohio

[73] Assignee: PPG Industries, Inc., Pittsburgh, Pa.

[21] Appl. No.: 859,271

[22] Filed: May 2, 1986

Related U.S. Application Data

[63] Continuation of Ser. No. 698,492, Feb. 5, 1985, abandoned, which is a continuation-in-part of Ser. No. 619,443, Jun. 11, 1984, abandoned, which is a continuation-in-part of Ser. No. 491,949, May 5, 1983, abandoned.

[51] Int. Cl.[4] .................. C07D 413/04; A01N 43/80
[52] U.S. Cl. ...................................... 71/92; 548/245; 548/246
[58] Field of Search ...................... 548/245, 246, 247; 71/88, 92

[56] References Cited

U.S. PATENT DOCUMENTS

| 4,028,376 | 6/1977 | Yukinaga et al. | 548/247 |
| 4,268,679 | 5/1981 | Lavanish | 548/247 |
| 4,345,936 | 8/1982 | Thibault et al. | 548/319 |
| 4,354,030 | 10/1982 | Burow et al. | 548/247 |

FOREIGN PATENT DOCUMENTS 2881   7/1979   European Pat. Off. ............ 548/247

Primary Examiner—Robert Gerstl
Attorney, Agent, or Firm—Edward J. Whitfield

[57] ABSTRACT

This invention relates to certain 3-isoxazolyl-2-imidazolidinone derivatives, namely 3-[5- or 3-substituted -3- or -5-isoxazolyl]-1-,4- or 5-substituted-2-imidazolidinones and the use thereof for preemergence or post-emergence control of noxious plants, i.e., weeds.

5 Claims, No Drawings

HERBICIDALLY ACTIVE 3-ISOXAZOLYL-2-IMIDAZOLIDINONE DERIVATIVES

CROSS-REFERENCE TO RELATED APPLICATION

This application is a continuation of application Ser. No. 698 492 filed Feb. 5, 1985 which is a continuation-in-part of application Ser. No. 619,443 filed June 11, 1984, which is a continuation-in-part of application Ser. No. 491,949 filed May 5, 1983, all since abandoned.

FIELD OF THE INVENTION

This invention relates to certain 3-isoxazolyl-2-imidazolidinone derivatives, namely 3-[5- or 3-substituted-3- or -5-isoxazolyl]-1-,4- or 5-substituted-2-imidazolidinones and the use thereof for preemergence or postemergence control of noxious plants, i.e., weeds.

DESCRIPTION OF THE INVENTION

This invention provides herbicidally active 3-[5- or 3-substituted-3- or -5-isoxazolyl]-1-,4- or 5-substituted-2-imidazolidinones represented by the Formula I:

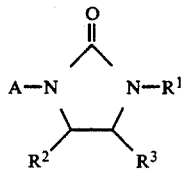

wherein A is

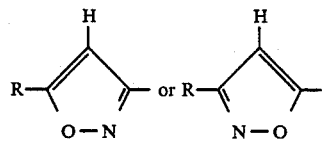

where
R is an alkyl of up to six carbon atoms, an alkenyl of up to five carbon atoms, an alkynyl of up to five carbon atoms, a cycloalkyl selected from the group consisting of cyclopropyl, cyclobutyl, cyclopentyl, and cyclohexyl, a haloalkyl of up to six carbon atoms, —R$^4$—O—R$^5$ or R$^4$—S—R$^5$, where R$^4$ is an alkylene of up to six carbon atoms and R$^5$ is an alkyl of up to six carbon atoms,

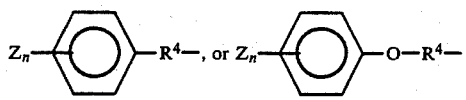

where Z is nitro (—NO$_2$), chloro (—Cl), bromo (—Br), fluoro (—F), or R$^5$, and n is 0, 1, 2 or 3; R$^1$ is an alkyl of up to three carbon atoms, or allyl; and R$^2$ and R$^3$ are selected from hydrogen or —SR$^6$ wherein R$^6$ is up to C$_{10}$ alkyl, haloalkyl, cyanoalkyl, hydroxyalkyl, sulfonylated alkyl, cycloalkyl, oxoalkyl, alkoxyalkyl, carboxalkyl, alkoxycarbonylalkyl, aryl or arylalkyl or aryl or arylalkyl substituted with hydroxy, halo, nitro or cyano, provided that at least one of R$^2$ or R$^3$ is —SR$^6$.

Although any compound within the scope of Formula I is believed to have herbicidal activity in accordance with this invention, preferred compounds are those wherein R is lower alkyl, especially tertiary butyl, R$^1$ is alkyl, especially methyl and R$^2$ is —SR$^6$ wherein R$^6$ is lower alkyl. It is of course to be understood that the stereo isomers of Formula I compound are also within the scope of this invention.

The compounds of this invention can be readily synthesized using available starting materials and using techniques known to the art. For example, Formula I compounds wherein R$^2$ or R$^3$ are —SR$^6$ may be prepared by reacting an appropriately substituted thiol with a compound of the Formula II:

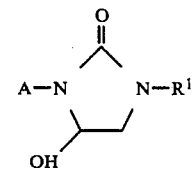

wherein A and R$^1$ are as previously defined. Compounds of the Formula II are described, for example in U.S. Pat. No. 4,268,679.

The following Examples are illustrative of the preparation of certain specific compounds of this invention.

EXAMPLE I

Preparation of 3-(5-t-butyl-3-isoxazolyl)-1-methyl-4- and 5-n-butylthio-2-imidazolidinone To a flask provided with a reflux condenser was charged 6.0 grams of 3-(5-t-butyl-isoxazolyl)-1-methyl-4-hydroxy-2-imidzaolidinone, 0.2 gram of p toluene sulfonic acid, 7.0 milliliters of butanethiol and 300 milliliters of benzene. The reaction mixture was heated to reflux and maintained at reflux for about 2½ hours, the progress of the reaction being monitored by TLC. The reaction mixture was then cooled, transferred to a separatory funnel and washed consecutively with 3×70 milliliter portions of saturated sodium bicarbonate solution and 3×50 milliliter portions of water. The organic layer was dried over anhydrous sodium sulfate and stripped of solvent affording 7.5 grams of colorless gummy liquid, which was purified by column chromatography. More particularly, the product was dissolved in methylene chloride and adsorbed onto 145 grams of silica gel wet-packed with methylene chloride into a 2.5×58 centimeter column. The column was eluted with methylene chloride and 4:1 V/V methylene chloride:ethyl acetate and the eluent fractions (about 100 milliliters) were analyzed by TLC. Combination of appropriate fractions and evaporation of solvent afforded 2.5 grams of product identified as 3-(5-t-butyl-3-isoxazolyl)-1-methyl-5-n-butylthio-2-imidazolidinone and 0.4 gram of product identified as 3-(5-t-butyl-3-isoxazolyl)-1-methyl-4-n-butylthio-2-imidazolidinone.

EXAMPLE II

Preparation of 3-(5-t-butyl-3-isoxazolyl)-1-methyl-4-methylthio-2-imidazolidinone To a three-necked flask provided with a magnetic stirring bar, dry-ice/acetone condenser and a gas inlet tube were charged 70 grams of 3-(5-t-butyl-3-isoxazolyl)-1-methyl-4-hydroxy-2-imidazolidinone, 5.0 grams of p-toluene sulfonic acid and 700 milliliters of t-butanol. A slow stream of gaseous mercaptomethanol was introduced into the stirred reaction mixture, a total 54 grams of mercaptomethanol being added over a 3 hour period. After 17 hours stirring at room temperature. HPLC and TLC analyses indicated unreacted starting material as the major component. Stirring was continued an additional 24 hours after which time HPLC analysis indicated about 50 percent conversion of starting material to desired product. The reaction mixture was then neutralized by the additiono of 10 grams of potassium carbonate in 15 milliliters of water and excess mercaptomethanol was removed by bubbling nitrogen gas through the reaction mixture. Evaporation of solvent, afforded a semi-solid gummy residue. The residue was dissolved in methylene chloride and adsorbed onto 840 grams of silica gel in a two liter sintered glass funnel. The silica gel was eluted with hexane:methylene chloride, methylene chloride and methylene chloride:methanol and the eluent fractions (about 500 milliliters) were analyzed by TLC or HPLC. Combination of appropriate fractions afforded 58 grams of material identified as the desired product.

EXAMPLE III

Preparation of 3-(5-t-butyl-3-isoxazolyl)-1-methyl-4 and 5-thioacetic acid-2-imidazolidinone A mixture of 3.2 grams of 3-(5-t-butyl-3-isoxazolyl)-1-methyl-4-hydroxy-2-imidazolidinone, 3.0 grams of mercaptoacetic acid, 0.2 gram of p-toluene sulfonic acid, 25 milliliters of anhydrous diethylether and 25 milliliters of anhydrous tetrahydrofuran was stirred under a nitrogen atmosphere at ambient temperature, for about 50 hours. After evaporation of solvent, the residue was taken-up in 200 milliliters of diethylether which was washed with a 25 milliliter portion of water and 4×30 milliliter portions of dilute aqueous sodium bicarbonate solution. The aqueous washings were combined, acidified and extracted with 4×50 milliliter portions of diethylether. The ether extracts were combined, washed with water, dried over anhydrous sodium sulfate and evaporated affording 3.0 grams of material identified as 3-(5-t-butyl-3-isoxazolyl)-1-methyl-4-thioaceticacid-2-imidazolidinone and 3-(5-t-butyl-3-isoxazolyl)-1-methyl-5-thioaceticacid-2-imidazolidinone in a weight ratio of 1.2:1.

EXAMPLE IV

Preparation of 3-(5-t-butyl-3-isoxazolyl)-1-methyl-4-thioethanol-2-imidazolidinone A mixture of 3.0 grams of 3-(5-t-butyl-3-isoxazolyl)-1-methyl-4-hydroxy-2-imidazolidinone, 3.0 grams of mercaptoethanol, 0.2 gram of p-toluene sulfonic acid, 20 milliliters of anhydrous diethylether and 20 milliliters of anhydrous tetrahydrofuran was stirred, under a nitrogen atmosphere at ambient temperature, for about 70 hours. The reaction mixture was then diluted with 150 milliliters of ethyl acetate, and the organic layer was washed with 30 milliliters of saturated aqueous sodium bicarbonate solution and 4×50 milliliter portions of water. The washed organic layer was then dried and evaporated affording 4.2 grams of colorless viscous liquid. Residual mercaptoethanol was removed by a high vacuum purge and the liquid material was purified by column chromatography. More particularly, the liquid material was dissolved in methylene chloride and adsorbed onto 150 grams of silica gel wet-packed with methylene chloride into a 3.5×30 centimeter column. The column was eluted with methylene chloride and methylene chloride:ethyl acetate. The eluent fractions (about 100 milliliters) were collected and analyzed by TLC. Combination of appropriate fractions and evaporation of solvent afforded 2.6 grams of the desired product.

Although preparation of certain compounds of the invention have been illustrated in some detail by the foregoing, it is to be understood that other compounds of the invention may be readily prepared by those skilled in the art using the same or similar syntheses and by varying the choice of starting materials.

Weed control in accordance with this invention is effected by applying to the growth medium before emergence of weeds therefrom or to the weed surfaces after their emergence from the growth medium a herbicidally effective amount of a compound of this invention. It is, of course, to be understood that the term "a compound of this invention" also includes mixtures of such compounds.

The term "herbicidally effective amount" is that amount of a compound of this invention required to so injure or damage weeds such that the weeds are incapable of recovering following application. The quantity of a compound of this invention applied in order to exhibit a satisfactory herbicidal effect may vary over a wide range and depends on a variety of factors, such as, for example, hardiness of a particular weed species, extent of weed infestation, climatic conditions, soil conditions, method of application, and the like. Typically, as little as one or less pound per acre of a compound of this invention would be expected to provide satisfactory weed control, although in some instances application rates in excess of one pound per acre; e.g., up to 5 or more pounds per acre might be required. Of course, the efficacy of a particular compound against a particular weed species may readily be determined by routine laboratory or field testing in a manner well known to the art. It is expected that satisfactory weed control can be had at a rate of application in the range of 0.25 to 1.0 pound per acre.

Of course, a compound of this invention can be formulated according to routine methods with any of several known and commonly used herbicidal diluents, adjuvants and carriers. The formulations can contain liquid carriers and adjuvants such as organic solvents, as well as emulsifiers, stabilizers, dispersants, suspending agents, spreaders, penetrants, wetting agents and the like. Typical carriers utilized in dry formulations include clay, talc, diatomaceous earth, silica and the like. Preferred formulations are those in the form of wettable powders, flowables, dispersible granulates or aqueous emulsifiable concentrates which can be diluted with water at the site of application. Also, dry formulations such as granules, dusts, and the like, may be used.

When desired, a compound of this invention can be applied in combination with other herbicidal agents in an effort to achieve even broader vegetative control. Typical herbicides which can be conveniently combined with Formula I compound include atrazine, hexazinone, metribuzin, ametryn, cyanazine, cyprazine, prometon, prometryn, propazine, simazine, terbutryn, propham, alachlor, acifluorfen, bentazon, metolachlor and N,N-dialkyl thiocarbamates such as EPTC, butylate or vernolate. These, as well as other herbicides described, for example, in the *Herbicide Handbook of the Weed Science Society of America,* may be used in combination with a compound or compounds of the invention. Typically such formulations will contain from about 5 to about 95 percent by weight of a compound of this invention.

The herbicidal formulations contemplated herein can be applied by any of several methods known to the art. Generally, the formulation will be surface applied as an aqueous spray. Such application can be carried out by conventional ground equipment, or if desired, the sprays can be aerially applied. Soil incorporation of such surface applied herbicides is accomplished by natural leaching, and is of course facilitated by natural rainfall and melting snow. If desired, however, the herbicides can be incorporated into the soil by conventional tillage means.

Compounds of this invention are believed effective for preemergence or postemergence control of a wide variety of broadleaf and grassy weeds. Typical of the various species of vegetative growth that may be controlled, combated, or eliminated are, for example, annuals such as pigweed, lambsquarters, foxtail, crabgrass, wild mustard, field pennycress, ryegrass, goose grass, chickweed, wild oats, velvetleaf, purslane, barnyardgrass, smartweed, knotweed, cocklebur, kochia, medic, ragweed, hemp nettle, spurrey, pondweed, carpetweed, morningglory, ducksalad, cheatgrass, fall panicum, jimsonweed, witchgrass, watergrass, wild turnip, and similar annual grasses and weeds. Biennials that may be controlled include wild barley, campion, burdock, bull thistle, roundleaved mallow, purple star thistle, and the like. Also controlled by the compounds of this invention are perennials such as quackgrass, Johnsongrass, Canada thistle, curly dock, field chickweed, dandelion, Russian knapweed aster, horsetail ironweed, sesbania, cattail, wintercress, horsenettle, nutsedge, milkweed, sicklepod, and the like.

The compounds prepared as described in the Examples were individually tested for herbicidal efficacy, against a variety of broadleaf and grassy weed species, under controlled laboratory conditions of light, humidity and temperature. Solvent solutions of said compounds were applied, both preemergence and postemergence, to test flats containing the various weed species, and herbicidal efficacy was determined by visual inspection, periodically after application of the compounds. Herbicidal efficacy was determined on a linear scale of from 0 (no injury) to 10 (all plants dead).

For example, the 4-n-butylthio compound prepared as described in Example I, when applied preemergence at a rate of 1.0 pound per acre, was found effective in controlling teaweed, jimsonweed, wild mustard, coffeeweed, velvetleaf, tall morningglory, yellow foxtail, large crabgrass, Johnsongrass and wild oats, herbicidal injury ratings of from 8 to 10 being determined 21 days following application.

The said Example I compound was also observed to be effective in controlling jimsonweed, wild mustard, coffeeweed and tall morningglory when applied postemergence at a rate of 1.0 pound per acre.

Similar herbicidal activities were observed for the compounds prepared as described in Example III and IV.

The herbicidal activity of the compound prepared as described in Example II was directly compared with the corresponding 4-methoxy derivative, i.e., the compound, 3-(5-t-butyl-3-isoxaozlyl)-1-methyl-4-methoxy-2-imidazolidinone, by applying a solvent solution of each compound preemergence at a rate of 0.25 pound per acre to a variety of broadleaved and grassy weed species, under the same controlled laboratory conditions of light, humidity and temperature, the following herbicidal injury ratings being determined 21 days following applications:

| Weed | Herbicidal Injury Rating Compound | |
|---|---|---|
| | 4-methylthio | 4-methoxy |
| Teaweed | 10 | 0 |
| Jimsonweed | 7 | 0 |
| Wild Mustard | 10 | 2 |
| Yellow nutsedge | 2 | 0 |
| Yellow foxtail | 5 | 0 |
| Large crabgrass | 2 | 1 |
| Johnsongrass | 8 | 0 |
| Coffeeweed | 10 | 2 |
| Velvet leaf | 10 | 0 |
| Tall morningglory | 10 | 2 |
| Wild oats | 10 | 2 |
| Barnyardgrass | 10 | 1 |

As the foregoing shows, the invention compound is significantly more herbicidally active than the comparison compound when applied preemergence at the rate of 0.25 pounds per acre, even though the compounds differ only in the nature of the substituent at the 4-position of the imidazolidinone ring, the invention compound having an —SCH$_3$ substituent, the comparison compound having an —OCH$_3$ substituent.

Although the invention has been described in considerable detail by the foregoing, it is to be understood that many variations may be made therein by those skilled in the art without departing from the spirit and scope thereof as defined by the appended claims.

We claim:

1. A compound of the formula:

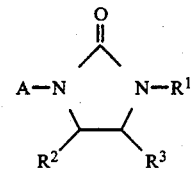

wherein A is

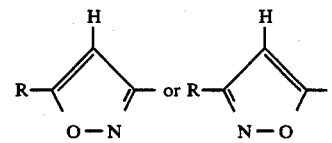

where
R is an alkyl of up to six carbon atoms, an alkenyl of up to five carbon atoms, an alkynyl of up to five carbon atoms, a cycloalkyl selected from the group consisting of cyclopropyl, cyclobutyl, cyclopentyl, and cyclohexyl, a haloalkyl of up to six carbon atoms, —R$^4$—O—R$^5$ or —R$^4$—S—R$^5$, where R$^4$ is an alkylene of up to six carbon atoms and R$^5$ is an alkyl of up to six carbon atoms,

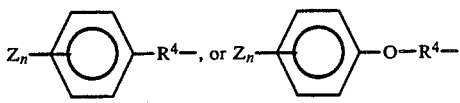

where Z is nitro (—NO$_2$), chloro (—Cl), bromo (—Br), fluoro (—F), or R$^5$, and n is 0, 1, 2 or 3; R$^1$ is an alkyl of up to three carbon atoms, or allyl; and R$^2$ and R$^3$ are selected from hydrogen or —SR$^6$ wherein R$^6$ is up to C$_{10}$ alkyl, haloalkyl, cyanoalkyl, hydroxyalkyl, sulfonylated alkyl, cycloalkyl, oxoalkyl, alkoxyalkyl, carboxyalkyl, alkoxycarbonylalkyl, aryl or arylalkyl or aryl or arylalkyl substituted with hydroxy, halo, nitro or cyano, provided that at least one of R$^2$ or R$^3$ is —SR$^6$.

2. A compound of claim 1 wherein R is lower alkyl, R$^1$ is lower alkyl and R$^2$ is —SR$^6$ wherein R$^6$ is lower alkyl.

3. A compound of claim 2 selected from 3-(5-t-butyl-3-isoxazolyl)-1-methyl-4-n-butylthio-2-imidazolidone or 3-(5-t-butyl-3-isoxazolyl)-1-methyl-4-methylthio-2-imidazolidinone.

4. A herbicidal composition containing a compound or mixture of compounds defined in claim 1 and an agronomically acceptable carrier.

5. The method of controlling the growth of weeds wherein a herbicidally effective amount of herbicide is applied to a growth medium prior to emergence of weeds therefrom or to the weeds subsequent to emergence from the growth medium wherein the improvement resides in using as the herbicide a compound or mixture of compounds as defined in claim 1.

* * * * *